US012570682B2

(12) United States Patent
Zhang et al.

(10) Patent No.: US 12,570,682 B2
(45) Date of Patent: Mar. 10, 2026

(54) METHOD FOR INCREASING BULK DENSITY OF NICOTINAMIDE MONONUCLEOTIDE CRYSTAL AND CRYSTAL THEREOF

(71) Applicants: BONTAC BIO-ENGINEERING (SHENZHEN) CO., LTD, Shenzhen (CN); ZHONGSHAN BONTAC BIO-TECHNOLOGY CO., LTD, Zhongshan (CN)

(72) Inventors: Zhang Zhang, Shenzhen (CN); Ming Chen, Shenzhen (CN); Chunliang Zhang, Shenzhen (CN)

(73) Assignee: BONTAC BIO-ENGINEERING (SHENZHEN) CO., LTD, Shenzhen (CN)

( * ) Notice: Subject to any disclaimer, the term of this patent is extended or adjusted under 35 U.S.C. 154(b) by 703 days.

(21) Appl. No.: 17/918,701

(22) PCT Filed: Nov. 8, 2021

(86) PCT No.: PCT/CN2021/129252
§ 371 (c)(1),
(2) Date: Oct. 13, 2022

(87) PCT Pub. No.: WO2023/077503
PCT Pub. Date: May 11, 2023

(65) Prior Publication Data
US 2024/0218007 A1 Jul. 4, 2024

(51) Int. Cl.
C07H 19/048 (2006.01)
C07H 1/06 (2006.01)
(52) U.S. Cl.
CPC ............. C07H 19/048 (2013.01); C07H 1/06 (2013.01)

(58) Field of Classification Search
CPC ...... C07H 19/048; C07H 1/06; C07B 2200/13
See application file for complete search history.

(56) References Cited

FOREIGN PATENT DOCUMENTS

| | | |
|---|---|---|
| CN | 108697722 A | 10/2018 |
| CN | 112694505 A | 4/2021 |
| CN | 112870979 A | 6/2021 |
| CN | 113402570 A | 9/2021 |
| CN | 113402575 A | 9/2021 |

OTHER PUBLICATIONS

CN113402570a, machine translation, Sep. 17, 2021. (Year: 2021).*

* cited by examiner

*Primary Examiner* — Layla D Berry
(74) *Attorney, Agent, or Firm* — MUNCY, GEISSLER, OLDS & LOWE, P.C.

(57) ABSTRACT

The present disclosure provides a method for increasing the bulk density of a nicotinamide mononucleotide crystal and a crystal thereof. The method includes: dissolving nicotinamide mononucleotide in water to obtain an aqueous solution of nicotinamide mononucleotide; performing vacuum concentration or freeze drying on the aqueous solution of nicotinamide mononucleotide to obtain a semi-solid with a water content equal to or less than 15%; adding a solventing-out agent dropwise to the semi-solid under stirring, and meanwhile, performing cooling at a rate of 1-15° C./h to a crystallization end temperature of 5-18° C.; and after a crystal is completely precipitated, performing filtration and drying on the crystal to obtain a nicotinamide mononucleotide crystal with increased bulk density. An NMN crystal of a bulk structure can be prepared by the method, and compared with existing NMN crystals, the bulk density of the NMN crystal is doubled.

10 Claims, 1 Drawing Sheet

METHOD FOR INCREASING BULK DENSITY OF NICOTINAMIDE MONONUCLEOTIDE CRYSTAL AND CRYSTAL THEREOF

FIELD OF TECHNOLOGY

The present disclosure relates to the technical field of preparation of compound crystals, and in particular to a method capable of increasing the bulk density of a nicotinamide mononucleotide crystal and a nicotinamide mononucleotide crystal prepared by the method.

BACKGROUND

Nicotinamide mononucleotide (NMN for short) is a biochemical substance inherent in biological cells. It may be adenylated by nicotinamide nucleotide adenosyltransferase in the cells to form an important substance-nicotinamide adenine dinucleotide (NAD for short, also known as coenzyme I, existing in all the cells, taking part in thousands of biocatalytic reactions, and playing an important role in the generation of biological cell energy) that the biological cells depend on for survival. NMN is a direct precursor of NAD. As an important intermediate of an NAD salvage synthesis pathway in biological cells, its level in the biological cells directly affects the concentration of NAD.

Studies have found that supplementing NMN in vitro is a most ideal way to increase the concentration of NAD in cells. In addition, it has also been found that supplementing NMN in vitro may achieve many health care effects of delaying aging, treating Parkinson's and other geriatric diseases, regulating insulin secretion, affecting mRNA expression and the like. Besides, more and more new medical uses of NMN are being reported. In addition, with the news of Li Ka-shing's investment in "elixir" NMN, the NMN has become a favorite for a while and has been favored by many capitals, and the general public is also rushing to pursue NMN medicines or health care products. As a result, the demand for the NMN medicines or health care products is increasing day by day.

At present, NMN in a crystal form is generally used as a raw material to produce NMN medicines or health care products. Two crystal forms of β-nicotinamide mononucleotide published in a Chinese patent application CN108697722A are most commonly used at present, including anhydrous crystals (form 1) and dimethyl sulfoxide solvate crystals (form 2) respectively. However, the two crystals have a low bulk density of only about 0.2 g/ml. Thus, the two NMN crystals have poor fluidity, and as a result, the NMN medicines or health care products produced have large content/weight difference and inconsistent quality. Even worse, the content/weight difference is greater than 100%, and troubles are brought to pharmaceutical and health care product manufacturers.

In order to solve the above-mentioned technical problems, a Chinese patent application CN11269505A discloses a method for preparing high-density NMN. The method includes: continuously adding a poor solvent to an aqueous solution of NMN to form a water-containing NMN oily layer: repeatedly beating the oily layer with the poor solvent several times to reduce the water content in the oily layer and slowly convert the oily layer into a white powder; and performing filtration, drying, pulverization with a particle swing machine, and sieving with a 40-80 mesh sieve to obtain NMN with high bulk density. According to embodiment data, it is shown that the NMN prepared by this method has a bulk density of 0.52 g/ml and a tap density of 0.71 g/ml. It can be seen that compared with the commonly used NMN crystals in form 1 and form 2, the bulk density of NMN prepared by this method is indeed greatly improved. However, from an attached electron microscope image, it can be seen that an NMN crystal prepared is of a rod-like structure. It is well known that the bulk density is closely related to the crystal shape, and a bulk crystal has higher bulk density than a rod-shaped crystal. Therefore, when an NMN crystal can be converted into a bulk structure, the bulk density of the NMN crystal can be further improved, so that the technical problems, such as large content/weight difference and inconsistent quality of NMN medicines or health care products due to poor fluidity of NMN crystals, can be better solved.

SUMMARY

In view of the deficiencies mentioned in the above background, an objective of the present disclosure is to develop a method for increasing the bulk density of a nicotinamide mononucleotide crystal, in order to obtain a nicotinamide mononucleotide crystal with a bulk structure, so that the technical problems, such as large content/weight difference and inconsistent quality of NMN medicines or health care products due to poor fluidity of existing NMN crystals, are solved.

To achieve the above objective, the present disclosure first provides a method for increasing the bulk density of a nicotinamide mononucleotide crystal. The method comprises the following steps: 1) dissolving nicotinamide mononucleotide in water to obtain an aqueous solution of nicotinamide mononucleotide: 2) performing vacuum concentration or freeze drying on the aqueous solution of nicotinamide mononucleotide to obtain a semi-solid with a water content equal to or less than 15%: 3) adding a solventing-out agent dropwise to the semi-solid under stirring, and meanwhile, performing cooling at a rate of 1-15° C./h to a crystallization end temperature of 5-18° C.; and 4) after a crystal is completely precipitated, performing filtration and drying on the crystal to obtain a nicotinamide mononucleotide crystal with increased bulk density.

The aqueous solution of nicotinamide mononucleotide usually has a pH value of 2.0-4.0. It is found by the inventor that in the method for increasing the bulk density of a nicotinamide mononucleotide crystal provided in the present disclosure, a change of the pH value of the aqueous solution of nicotinamide mononucleotide has great influence on the bulk density of the nicotinamide mononucleotide crystal finally obtained, and especially when the pH value is adjusted to 4.5-6.5, the bulk density of the nicotinamide mononucleotide crystal may be significantly increased. Therefore, preferably, the method for increasing the bulk density of a nicotinamide mononucleotide crystal provided in the present disclosure further comprises: before step 2), adjusting the pH value of the aqueous solution of nicotinamide mononucleotide to 4.5-6.5.

More preferably, in the method for increasing the bulk density of a nicotinamide mononucleotide crystal provided in the present disclosure, the pH value of the aqueous solution of nicotinamide mononucleotide is adjusted by using sodium dihydrogen phosphate and disodium hydrogen phosphate.

According to the method for increasing the bulk density of a nicotinamide mononucleotide crystal provided in the present disclosure, in step 2), the so-called semi-solid, whose physical professional name is quasi-solid, is also called amorphous solid, which is different from a traditional crystalline solid, and is disordered at the microscopic scale.

Preferably, according to the method for increasing the bulk density of a nicotinamide mononucleotide crystal provided in the present disclosure, in step 2), the vacuum concentration is performed at a temperature of 40-50° C. On the one hand, the temperature ensures high concentration efficiency and avoids the risk of degrading nicotinamide mononucleotide at high temperature. On the other hand, the temperature provides a precondition for subsequent cooling and crystallization processes, and is conducive to complete precipitation of crystals.

More preferably, according to the method for increasing the bulk density of a nicotinamide mononucleotide crystal provided in the present disclosure, in step 2), a vacuum degree during the vacuum concentration is controlled within a range of 0.07-0.10 MPa.

Preferably, according to the method for increasing the bulk density of a nicotinamide mononucleotide crystal provided in the present disclosure, in step 2), the freeze drying is performed at a start temperature of −45±5° C. and an end temperature of 25-30° C.

According to the method for increasing the bulk density of a nicotinamide mononucleotide crystal provided in the present disclosure, in step 2), it is found by the inventor that when the aqueous solution of nicotinamide mononucleotide is concentrated to a water content of 5% and then continuously concentrated to reduce the water content, the bulk density of the obtained nicotinamide mononucleotide crystal is less increased. Therefore, considering the time and economic cost, preferably, the vacuum concentration is performed on the aqueous solution of nicotinamide mononucleotide to obtain a semi-solid with a water content of 5-15%.

Preferably, according to the method for increasing the bulk density of a nicotinamide mononucleotide crystal provided in the present disclosure, in step 3), the solventing-out agent is at least one selected from the group consisting of methanol, ethanol, and acetone. These three solventing-out agents can make the nicotinamide mononucleotide crystal rapidly and completely precipitated, and are low in cost and easy to obtain.

Preferably, according to the method for increasing the bulk density of a nicotinamide mononucleotide crystal provided in the present disclosure, in step 3), the solventing-out agent whose volume is 4-6 times a weight of the semi-solid is added dropwise.

According to the method for increasing the bulk density of a nicotinamide mononucleotide crystal provided in the present disclosure, in step 3), it is found by the inventor through a comparative study that the dropping rate of the solventing-out agent has great influence on the bulk density of the crystal. Therefore, preferably, the dropping rate of the solventing-out agent is controlled to be 50-200 ml/h. This range can ensure that the finally obtained crystal is of a bulk structure, so that a crystal with the highest bulk density is obtained.

Preferably, according to the method for increasing the bulk density of a nicotinamide mononucleotide crystal provided in the present disclosure, when the solventing-out agent is added dropwise, a stirring rate is maintained within a range of 50-500 rpm.

According to the method for increasing the bulk density of a nicotinamide mononucleotide crystal provided in the present disclosure, in step 3), it is found by the inventor that when the cooling is performed at a rate of less than 5° C./h, the bulk density of the obtained nicotinamide mononucleotide crystal is not changed great as the cooling rate is continuously reduced. Therefore, considering the time and economic cost, preferably, the cooling is performed at a rate of 5-15° C./h.

According to the method for increasing the bulk density of a nicotinamide mononucleotide crystal provided in the present disclosure, in step 3), it is found by the inventor that when the crystallization end temperature is reduced to less than 10° C., the bulk density of the obtained nicotinamide mononucleotide crystal is not changed great as the crystallization end temperature is continuously reduced. Therefore, considering the time and economic cost, preferably, the crystallization end temperature is 10-18° C.

In addition, the present disclosure further provides a nicotinamide mononucleotide crystal. The crystal is of a bulk structure.

Preferably, the nicotinamide mononucleotide crystal provided in the present disclosure is prepared by the method for increasing the bulk density of a nicotinamide mononucleotide crystal provided in the present disclosure.

The present disclosure has the following beneficial effects.

The present disclosure provides a method capable of significantly increasing the bulk density of a nicotinamide mononucleotide crystal and a nicotinamide mononucleotide crystal prepared by the method. Compared with the prior art, the nicotinamide mononucleotide crystal prepared by the method is of a bulk structure. Compared with existing nicotinamide mononucleotide crystals with rod-like or even needle-like structures, the particle size is significantly increased, the bulk density is doubled, greater advantages in production and processing of NMN medicines or health care products are achieved, and the technical problems, such as large content/weight difference and inconsistent quality of NMN medicines or health care products due to poor fluidity of NMN crystals, can be better solved.

DESCRIPTION OF THE EMBODIMENTS

The present disclosure is further described in detail below with reference to the accompanying drawings and specific examples. The following examples are to explain the present disclosure. The present disclosure is not limited to the following examples.

Unless otherwise specified, reagents used in the following examples are purchased from the market.

Bulk densities mentioned below are all loose bulk densities, and specific values are measured by the following method: taking an object to be tested, sieving the object (1.00 mm No. 18), accurately weighing the object, slowly pouring the object into a glass graduated cylinder, scraping the top, recording an apparent volume, and calculating the bulk density; and taking 3 same samples for parallel measurement, recording the readings, and using an average value as a measurement result.

Figure 1:
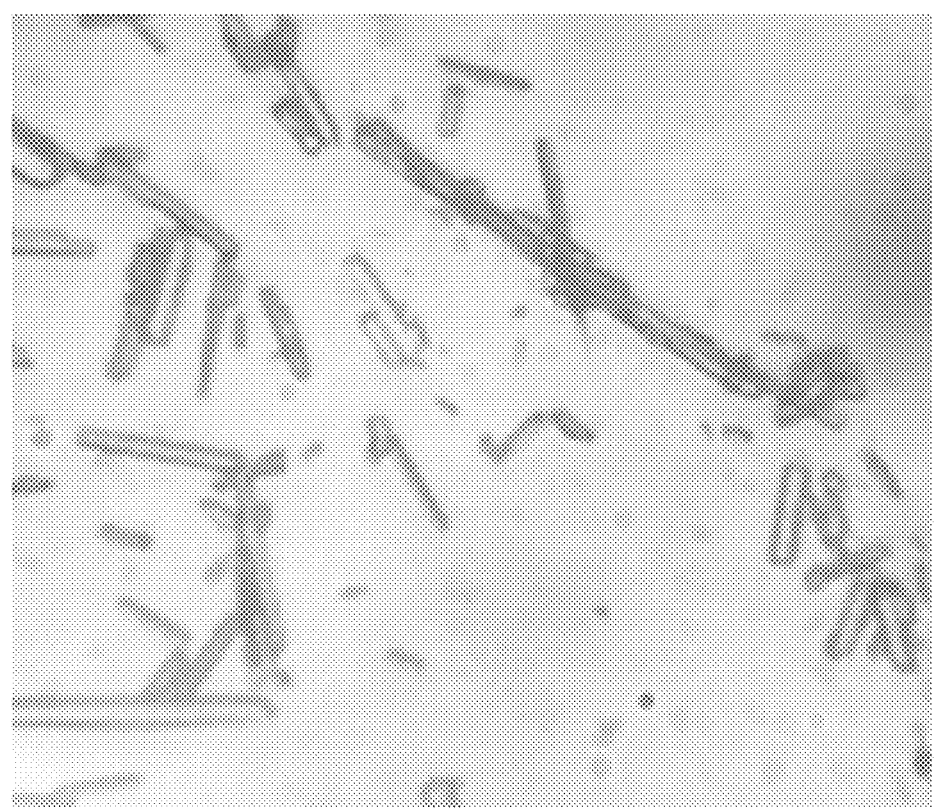
FIG. 1 is an electron microscope image of a nicotinamide mononucleotide anhydrous crystal prepared with reference to a method disclosed in Example 1 of a Chinese patent application CN108697722A.

A nicotinamide mononucleotide anhydrous crystal prepared with reference to a method disclosed in Example 1 of a Chinese patent application CN108697722A is used as a nicotinamide mononucleotide raw material in the following examples. The crystal is measured to have a bulk density of 0.20 g/ml, and an electron microscope image of the crystal is shown in FIG. 1.

Example 1

Study on a relationship between the water content of a semi-solid and the bulk density 20 g of a β-nicotinamide mononucleotide raw material was dissolved in 60 mL of water to obtain an aqueous solution of nicotinamide mononucleotide, and the aqueous solution was measured to have a pH value of 3.5. Then, the aqueous solution was rapidly subjected to vacuum concentration in a water bath at 45° C. to obtain semi-solids with different water contents as shown in Table 1, where a vacuum degree was controlled to 0.07 MP. Next, anhydrous ethanol whose volume was 5 times a weight of the semi-solids was added dropwise to the semi-solids with different water contents at a constant rate of 100 ml/h under stirring at a rate of 200 rpm, and meanwhile, cooling was performed at a rate of 10° C./h to a crystallization end temperature of 10° C. Crystal growing was performed for 3 h, and crystals were filtered and dried to obtain nicotinamide mononucleotide crystals.

Figure 2:
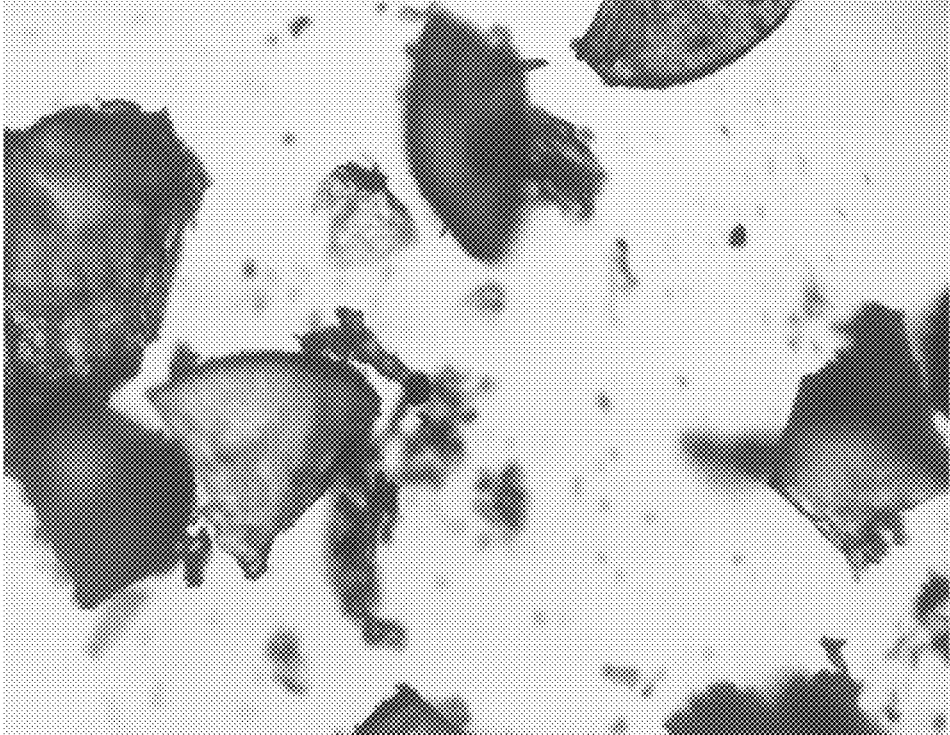
FIG. 2 is an electron microscope image of a nicotinamide mononucleotide crystal prepared by a method provided in the present disclosure.

The nicotinamide mononucleotide crystals obtained under the above different conditions were measured to obtain bulk densities respectively, and measured results are shown in Table 1. An electron microscope image of the nicotinamide mononucleotide crystal corresponding to the semi-solid with a water content of 15% is shown in FIG. 2.

TABLE 1

| Water content of a semi-solid | Bulk density |
|---|---|
| 75% | 0.26 |
| 50% | 0.33 |
| 35% | 0.44 |
| 25% | 0.56 |
| 20% | 0.67 |
| 15% | 0.77 |
| 10% | 0.89 |
| 5% | 1.03 |
| 1% | 1.05 |

Example 2

Study on a relationship between a cooling method and the bulk density 20 g of a β-nicotinamide mononucleotide raw material was dissolved in 60 mL of water to obtain an aqueous solution of nicotinamide mononucleotide, and the aqueous solution was measured to have a pH value of 3.5. Then, the aqueous solution was rapidly subjected to vacuum concentration in a water bath at 45° C. to obtain a semi-solid with a water content of 10%, where a vacuum degree was controlled to 0.07 MP. Next, anhydrous ethanol whose volume was 5 times a weight of the semi-solid was added dropwise to the semi-solid at a constant rate of 100 ml/h under stirring at a rate of 200 rpm, and meanwhile, cooling was performed at different cooling rates as shown in Table 2 to different crystallization end temperatures as shown in Table 2. Crystal growing was performed for 3 h, and crystals were filtered and dried to obtain nicotinamide mononucleotide crystals.

The nicotinamide mononucleotide crystals obtained under the above different conditions were measured to obtain bulk densities respectively, and measured results are shown in Table 2.

TABLE 2

| Cooling rate | Crystallization end temperature | Bulk density |
|---|---|---|
| 20 | 10 | 0.35 |
| 15 | 25 | 0.34 |
| 15 | 18 | 0.82 |
| 15 | 10 | 0.84 |
| 15 | 8 | 0.84 |
| 10 | 18 | 0.84 |
| 10 | 10 | 0.89 |
| 10 | 5 | 0.88 |
| 5 | 18 | 0.88 |
| 5 | 10 | 0.92 |
| 5 | 5 | 0.92 |
| 3 | 10 | 0.93 |
| 1 | 10 | 0.93 |
| 1 | 18 | 0.88 |

Example 3

Study on a relationship between the pH value of an aqueous solution of nicotinamide mononucleotide and the bulk density 20 g of a β-nicotinamide mononucleotide raw material was dissolved in 60 mL of water to obtain an aqueous solution of nicotinamide mononucleotide, and the pH value of the aqueous solution of nicotinamide mononucleotide was adjusted to different values as shown in Table 3 by adding sodium dihydrogen phosphate and disodium hydrogen phosphate. Then, the aqueous solutions with adjusted pH values were rapidly subjected to vacuum concentration in a water bath at 45° C. to obtain semi-solids with a water content of 10%, where a vacuum degree was controlled to 0.07 MP. Next, anhydrous ethanol whose volume was 5 times a weight of the semi-solids was added dropwise to the semi-solids at a constant rate of 100 ml/h under stirring at a rate of 200 rpm, and meanwhile, cooling was performed at a rate of 10° C./h to a crystallization end temperature of 10° C. Crystal growing was performed for 3 h, and crystals were filtered and dried to obtain nicotinamide mononucleotide crystals.

The nicotinamide mononucleotide crystals obtained under the above different conditions were measured to obtain bulk densities respectively, and measured results are shown in Table 3.

TABLE 3

| pH value of an aqueous solution of NMN | Bulk density |
|---|---|
| 3.5 | 0.89 |
| 4.5 | 1.08 |
| 5.0 | 1.09 |
| 5.5 | 1.09 |
| 6.0 | 1.07 |
| 6.5 | 1.08 |
| 7.0 | 0.81 |

Example 4

Nicotinamide mononucleotide crystal prepared by the method for increasing the bulk density of a nicotinamide mononucleotide crystal provided in the present disclosure 20 g of a β-nicotinamide mononucleotide raw material was dissolved in 60 mL of water to obtain an aqueous solution of nicotinamide mononucleotide, and the pH value of the aqueous solution of nicotinamide mononucleotide was adjusted to 5.0 by adding sodium dihydrogen phosphate and disodium hydrogen phosphate. Then, the aqueous solution with the adjusted pH value was rapidly subjected to vacuum concentration in a water bath at 40° C. to obtain a semi-solid with a water content of 15%, where a vacuum degree was controlled to 0.10 MP. Next, anhydrous acetone whose volume was 4 times a weight of the semi-solid was added dropwise to the semi-solid at a constant rate of 50 ml/h under stirring at a rate of 100 rpm, and meanwhile, cooling was performed at a rate of 5° C./h to a crystallization end temperature of 15° C. Crystal growing was performed for 3 h, and a crystal was filtered and dried to obtain a nicotinamide mononucleotide crystal. The crystal was measured to have a bulk density of 1.02 g/ml.

Example 5

Nicotinamide mononucleotide crystal prepared by the method for increasing the bulk density of a nicotinamide mononucleotide crystal provided in the present disclosure 20 g of a β-nicotinamide mononucleotide raw material was dissolved in 60 mL of water to obtain an aqueous solution of nicotinamide mononucleotide, and the pH value of the aqueous solution of nicotinamide mononucleotide was adjusted to 5.5 by adding sodium dihydrogen phosphate and disodium hydrogen phosphate. Then, the aqueous solution with the adjusted pH value was rapidly subjected to vacuum concentration in a water bath at 50° C. to obtain a semi-solid with a water content of 5%, where a vacuum degree was controlled to 0.07 MP. Next, a mixture of anhydrous acetone and anhydrous ethanol, whose volume was 6 times a weight of the semi-solid, was added dropwise to the semi-solid at a constant rate of 200 ml/h under stirring at a rate of 300 rpm, and meanwhile, cooling was performed at a rate of 15° C./h to a crystallization end temperature of 10° C. Crystal growing was performed for 3 h, and a crystal was filtered and dried to obtain a nicotinamide mononucleotide crystal. The crystal was measured to have a bulk density of 1.17 g/ml.

Nicotinamide mononucleotide crystal prepared by the method for increasing the bulk density of a nicotinamide mononucleotide crystal provided in the present disclosure

Example 6

20 g of a β-nicotinamide mononucleotide raw material was dissolved in 60 mL of water to obtain an aqueous solution of nicotinamide mononucleotide, and the pH value of the aqueous solution of nicotinamide mononucleotide was adjusted to 4.5 by adding sodium dihydrogen phosphate and disodium hydrogen phosphate. Then, the aqueous solution with the adjusted pH value was rapidly subjected to vacuum concentration in a water bath at 50° C. to obtain a semi-solid with a water content of 8%, where a vacuum degree was controlled to 0.07 MP. Next, a mixture of anhydrous methanol, anhydrous ethanol, and anhydrous acetone, whose volume was 5 times a weight of the semi-solid, was added dropwise to the semi-solid at a constant rate of 150 ml/h under stirring at a rate of 50 rpm, and meanwhile, cooling was performed at a rate of 5° C./h to a crystallization end temperature of 18° C. Crystal growing was performed for 3 h, and a crystal was filtered and dried to obtain a nicotinamide mononucleotide crystal. The crystal was measured to have a bulk density of 1.21 g/ml.

Example 7

Nicotinamide mononucleotide crystal prepared by the method for increasing the bulk density of a nicotinamide mononucleotide crystal provided in the present disclosure 20 g of a β-nicotinamide mononucleotide raw material was dissolved in 60 mL of water to obtain an aqueous solution of nicotinamide mononucleotide, and the pH value of the aqueous solution of nicotinamide mononucleotide was adjusted to 5.0 by adding sodium dihydrogen phosphate and disodium hydrogen phosphate. Then, the aqueous solution with the adjusted pH value was subjected to drying in a freezer dryer to obtain a semi-solid with a water content of 10%, where the drying was performed at a start temperature of −45° C. and an end temperature of 25° C. Next, anhydrous methanol whose volume was 5 times a weight of the semi-solid was added dropwise to the semi-solid at a constant rate of 150 ml/h under stirring at a rate of 50 rpm, and meanwhile, cooling was performed at a rate of 5° C./h to a crystallization end temperature of 18° C. Crystal growing was performed for 3 h, and a crystal was filtered and dried to obtain a nicotinamide mononucleotide crystal. The crystal was measured to have a bulk density of 0.95 g/ml.

Example 8

Nicotinamide mononucleotide crystal prepared by the method for increasing the bulk density of a nicotinamide mononucleotide crystal provided in the present disclosure 20 g of a β-nicotinamide mononucleotide raw material was dissolved in 60 mL of water to obtain an aqueous solution of nicotinamide mononucleotide, and the pH value of the aqueous solution of nicotinamide mononucleotide was adjusted to 5.0 by adding sodium dihydrogen phosphate and disodium hydrogen phosphate. Then, the aqueous solution with the adjusted pH value was subjected to drying in a freezer dryer to obtain a semi-solid with a water content of 5%, where the drying was performed at a start temperature of −45° C. and an end temperature of 30° C. Next, anhydrous methanol whose volume was 5 times a weight of the semi-solid was added dropwise to the semi-solid at a constant rate of 50 ml/h under stirring at a rate of 50 rpm, and meanwhile, cooling was performed at a rate of 5° C./h to a crystallization end temperature of 10° C. Crystal growing was performed for 3 h, and a crystal was filtered and dried to obtain a nicotinamide mononucleotide crystal. The crystal was measured to have a bulk density of 1.24 g/ml.

Comparative Example 1

20 g of β-nicotinamide mononucleotide raw material was dissolved in 60 mL of water to obtain an aqueous solution of nicotinamide mononucleotide, and the aqueous solution was measured to have a pH value of 3.5. Then, 110 ml of anhydrous ethanol was added dropwise to the aqueous solution at a constant rate of 100 ml/h under stirring at a rate of 200 rpm, and meanwhile, cooling was performed at a rate of 10° C./h to a crystallization end temperature of 10° C. Crystal growing was performed for 3 h, and a crystal was filtered and dried to obtain a nicotinamide mononucleotide crystal. The crystal was measured to have a bulk density of 0.23 g/ml.

Comparative Example 2

2.2 mL of water was added to 20 g of a β-nicotinamide mononucleotide raw material for uniform mixing to obtain a mixture with a water content of 10%. Then, 110 ml of anhydrous ethanol was added dropwise to the mixture at a constant rate of 100 ml/h under stirring at a rate of 200 rpm, and meanwhile, cooling was performed at a rate of 10° C./h to a crystallization end temperature of 10° C. Crystal growing was performed for 3 h, and a crystal was filtered and dried to obtain a nicotinamide mononucleotide crystal. The crystal was measured to have a bulk density of 0.20 g/ml.

Comparative Example 3

20 g of a β-nicotinamide mononucleotide raw material was dissolved in 60 mL of water to obtain an aqueous solution of nicotinamide mononucleotide, and the aqueous solution was measured to have a pH value of 3.5. Then, the aqueous solution was rapidly subjected to vacuum concentration in a water bath at 45° C. to obtain a semi-solid with a water content of 10%, where a vacuum degree was controlled to 0.07 MP. Next, after the semi-solid was placed to room temperature, anhydrous ethanol whose volume was 5 times a weight of the semi-solid was added dropwise to the semi-solid at a constant rate of 100 ml/h under stirring at a rate of 200 rpm. Crystal growing was performed for 3 h, and a crystal was filtered and dried to obtain a nicotinamide mononucleotide crystal. The crystal was measured to have a bulk density of 0.40 g/ml.

Comparative Example 4

20 g of a β-nicotinamide mononucleotide raw material was dissolved in 60 mL of water to obtain an aqueous solution of nicotinamide mononucleotide, and the pH value of the aqueous solution of nicotinamide mononucleotide was adjusted to 5.0 by adding sodium dihydrogen phosphate and disodium hydrogen phosphate. Then, the aqueous solution was rapidly subjected to vacuum concentration in a water bath at 45° C. to obtain a semi-solid with a water content of 10%, where a vacuum degree was controlled to 0.07 MP. Next, after the semi-solid was placed to room temperature, anhydrous ethanol whose volume was 5 times a weight of the semi-solid was added dropwise to the semi-solid at a constant rate of 100 ml/h under stirring at a rate of 200 rpm. Crystal growing was performed for 3 h, and a crystal was filtered and dried to obtain a nicotinamide mononucleotide crystal. The crystal was measured to have a bulk density of 0.56 g/ml.

The invention claimed is:

1. A method for increasing the bulk density of a nicotinamide mononucleotide crystal, comprising the following steps: 1) dissolving nicotinamide mononucleotide in water to obtain an aqueous solution of nicotinamide mononucleotide; 2) performing vacuum concentration or freeze drying on the aqueous solution of nicotinamide mononucleotide to obtain a semi-solid with a water content equal to or less than 15%; 3) adding a solventing-out agent dropwise to the semi-solid under stirring, and meanwhile, performing cooling at a rate of 1-15° C./h to a crystallization end temperature of 5-18° C.; and 4) after a crystal is completely precipitated, performing filtration and drying on the crystal to obtain a nicotinamide mononucleotide crystal with increased bulk density.

2. The method for increasing the bulk density of a nicotinamide mononucleotide crystal according to claim 1, further comprising: before step 2), adjusting the pH value of the aqueous solution of nicotinamide mononucleotide to 4.5-6.5.

3. The method for increasing the bulk density of a nicotinamide mononucleotide crystal according to claim 1, wherein in step 2), the vacuum concentration is performed at a temperature of 40-50° C.

4. The method for increasing the bulk density of a nicotinamide mononucleotide crystal according to claim 1, wherein in step 2), the freeze drying is performed at an end temperature of 25-30° C.

5. The method for increasing the bulk density of a nicotinamide mononucleotide crystal according to claim 1, wherein in step 2), the vacuum concentration is performed on the aqueous solution of nicotinamide mononucleotide to obtain a semi-solid with a water content of 5-15%.

6. The method for increasing the bulk density of a nicotinamide mononucleotide crystal according to claim 1, wherein in step 3), the solventing-out agent is at least one selected from the group consisting of methanol, ethanol, and acetone.

7. The method for increasing the bulk density of a nicotinamide mononucleotide crystal according to claim 1, wherein in step 3), the solventing-out agent whose volume is 4-6 times a weight of the semi-solid is added dropwise.

8. The method for increasing the bulk density of a nicotinamide mononucleotide crystal according to claim 1, wherein in step 3), the solventing-out agent is added dropwise at a rate of 50-200 ml/h.

9. The method for increasing the bulk density of a nicotinamide mononucleotide crystal according to claim 1, wherein in step 3), the cooling is performed at a rate of 5-15° C./h.

10. The method for increasing the bulk density of a nicotinamide mononucleotide crystal according to claim 1, wherein in step 3), the crystallization end temperature is 10-18° C.

* * * * *